(12) United States Patent
Blizzard et al.

(10) Patent No.: US 9,574,153 B1
(45) Date of Patent: Feb. 21, 2017

(54) COMPOSITIONS HAVING LUBRICANT PROPERTIES

(71) Applicants: John D Blizzard, Bay City, MI (US); Robert L McKellar, Midland, MI (US)

(72) Inventors: John D Blizzard, Bay City, MI (US); Robert L McKellar, Midland, MI (US)

(*) Notice: Subject to any disclaimer, the term of this patent is extended or adjusted under 35 U.S.C. 154(b) by 0 days.

(21) Appl. No.: 14/876,898

(22) Filed: Oct. 7, 2015

(51) Int. Cl.
*C07F 7/00* (2006.01)
*C10M 105/76* (2006.01)
*C07F 7/18* (2006.01)

(52) U.S. Cl.
CPC .......... *C10M 105/76* (2013.01); *C07F 7/1816* (2013.01)

(58) Field of Classification Search
CPC .................. C07F 7/10; C09J 183/08
USPC ......................................... 556/457
See application file for complete search history.

(56) References Cited

U.S. PATENT DOCUMENTS

2007/0036906 A1* 2/2007 Reeve .................... A01N 55/00
427/421.1

* cited by examiner

*Primary Examiner* — Porfirio Nazario Gonzalez
*Assistant Examiner* — Kofi Adzamli

(57) ABSTRACT

New compositions of matter that provide lubricant properties when cured into a coating on a substrate. The compositions are low molecular weight structured polysilicate compositions that have high silanol contents. The polysilicates are combined with a condensation catalyst and allowed to cure on the appropriate substrate. The cured coating has lubricant properties.

16 Claims, No Drawings

COMPOSITIONS HAVING LUBRICANT PROPERTIES

BACKGROUND OF THE INVENTION

This invention deals with new compositions of matter that provide lubricant properties when cured into a coating on a substrate.

There are many applications for lubricants and the majority of such applications are satisfied by the use of greases, oils, and such other lubricants. However, there are many applications where it is desirable that the lubricant not be a grease or liquid of any kind, such as oils.

Such applications are, for example, coating wire and cable to allow sufficient pull through when such wire and cable is installed in a building. Another application is a solid coating for arrow shafts such that the arrows can be easily removed from bales and targets.

Additional applications include process equipment that requires a solid lubricant, such as process equipment that is subjected to wear by solid materials. Such lubricant coatings should also have the benefit of anti-abrasion, anti-corrosion and or anti-erosion. Such equipment can be, for example, forming tools, extrusion and compounding equipment, size reduction and size classification equipment, engines, such as diesel, and turbines.

THE INVENTION

Thus what is disclosed and claimed herein is a composition of matter having the average general formula:

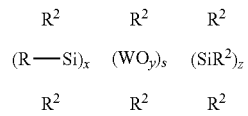

wherein the average molar ratio of x:y:z is 0.25-3:4:0.25-3, W is independently selected from the group consisting essentially of Si, Ti, and Zr, and Al; wherein each $R^1$ is an aryl group with the proviso that there is present at least one $R^1$ group; R is selected from the group consisting essentially of $R^1$, alkyl groups having 1 to 8 carbon atoms, each $R^2$ is a hydroxyl group, an aryl group, an alkoxy group having 1 to 8 carbon atoms, or an

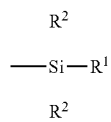

radical;
y has a value of 4;
s has an average value of about 1 to 5;
wherein $WO_y$ is derived from $W(OR^3)_4$ wherein $(OR^3)$ is independently selected from the group consisting of —$OCH_3$, —$OCH_2CH_3$, —$OCH(CH_3)_2$, —$O(CH_2)_3CH_3$, —$OCH_2CH(C_3)_2$, —O(2-ethylhexyl), acetoxy, and, oximo.

Another embodiment of this invention is a water solution of the composition described just Supra.

Still another embodiment of this invention is a water-alcohol solution of the composition described just Supra.

An additional embodiment is a cured coating having lubricant properties.

DETAILED DESCRIPTION OF THE INVENTION

The compositions of this invention are low molecular weight polysilicate compositions that have high silanol or alkoxy contents, that is, have a large number of silanols or alkoxy groups in the molecule. By "large number of silanols or alkoxy groups" it is meant that at least half of the Si atoms in the molecule are bonded by hydroxy groups when fully hydrolyzed.

One method for providing the materials of this invention comprises providing the components:

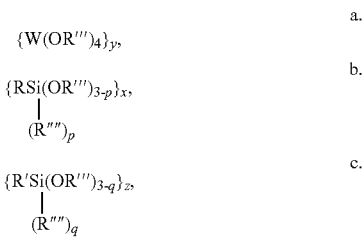

wherein the molar ratio of x:y:z is 0.25-3:4:0.25-3, p and q each independently have a value of 2 or less, R''' is the same as $R^3$; R'''' is independently selected from the methyl group or the phenyl group, and co-hydrolyzing the components in the presence of a predetermined amount of water, and a catalyst for hydrolysis and condensation.

The components

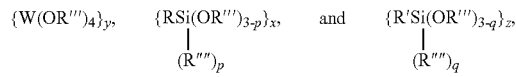

are commercially available from several sources.

By careful, controlled hydrolysis of the precursor monomers, one can obtain the materials of this invention at very low molecular weights, the detail of which can be found infra in the specification, and in the examples.

The materials have the average general formula

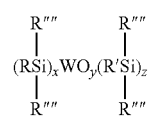

wherein R, R', R'''', W, x, y, and z all have the meanings set forth Supra, which is derived by the hydrolysis of the silane precursors

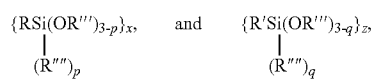

in conjunction with the orthosilicate, orthotitanate, orthozirconate or, orthoaluminate, having the general formula $\{W(OR''')_4\}_y$, wherein the molar ratio of x:y:z is 0.25-3:4:0.25-3, in a controlled manner to avoid random products.

This hydrolysis is carried out using a stoichiometric or less than stoichiometric amounts of water and a catalyst for hydrolysis. Using stoichiometric amounts of water, or, an amount of water less than stoichiometric, results in low molecular weight materials, which is one of the objectives of the method in this invention.

It is believed by the inventors herein that the key to this invention is the use of the molecule: $\{W(OR''')_4\}_y$ as the third component of this invention. W in the case of this invention is independently selected from the group consisting of Si, Ti, and Zr. Preferred for this invention is Si and Ti and most preferred is Si.

The (OR''') group is selected from the group consisting of —$OCH_3$, —$OCH_2CH_3$, —$OCH(CH_3)_2$, —$O(CH_2)_2$ $CH_3$, —$OCH_2CH(CH_3)_2$, —O(2-ethylhexyl), acetoxy, and, oximo. Preferred for this invention are the groups —$OCH_3$, —$OCH_2CH_3$, and —$OCH(CH_3)_2$, and most preferred are the —$OCH_3$ and —$OCH_2CH_3$ groups. Preferred orthosilicates and orthotitanates for this invention are $Si(OCH_2CH_3)_4$ and $Ti(OCH(CH_3)_2)_4$.

Stoichiometry is based on the number of hydrolysable groups on the combined components. The reaction is carried out in the presence of base or acid, with acid being the preferred catalyst. The acid catalysts are preferred to be HCl, phosphoric, and acetic acids, with HCl and phosphoric acids being most preferred.

Bases that are useable herein are amines, NaOH, KOH and the like and preferred for this invention is NaOH. The hydrolysis reaction is carried out by combining the components in a predetermined ratio and then adding predetermined amounts of acidic or basic water to the components at a controlled rate to form silanols from the alkoxy moieties. For some end use applications of the inventive materials, a slightly higher molecular weight (higher number of silanol reactive groups) is preferred and in this case, the silicate component is treated for a short period of time by acidic or basic water to cause the silicate component to hydrolyze and mildly condense before the other components are added.

By the preferred means, the following reaction sequence is achieved wherein Φ is the phenyl group:

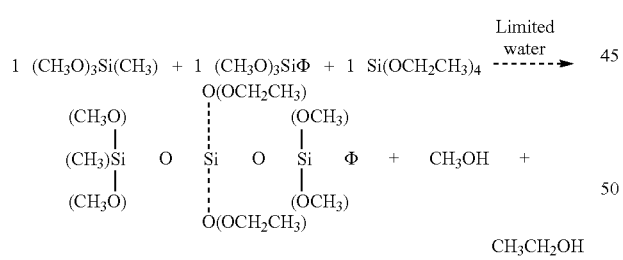

Subsequent predetermined additions of water would then result in materials having a portion of alkoxy groups and a portion of hydroxy groups on silicon, or if enough water is used, all of the alkoxy groups would hydrolyze and leave only hydroxy groups on silicon. For example,

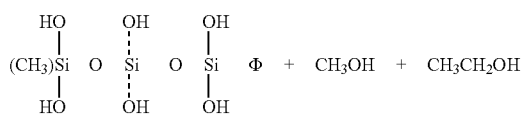

No heat is generally used in this reaction as higher temperatures (in excess of about 150° C.) may result in a gelation of the reaction mixture. Thus, the reactions are generally run at room temperature. There is a small exotherm from the hydrolysis reaction but the heat is not sufficient to provide problems with the resultant product. No solvents are required in this reaction, but it is within the scope of this invention to utilize solvents. It should be noted that the byproducts of the hydrolysis reaction are alcohol, acetic acid, or oxime. Typically, the products of this reaction do not need filtration.

As mentioned Supra, it is possible to enhance the molecular weight and thereby increase the amount of silanol functionality on the molecule by first mildly hydrolyzing the ortho precursor and then adding the remainder of the components.

Thus, a molecule having the following average formula may be obtained:

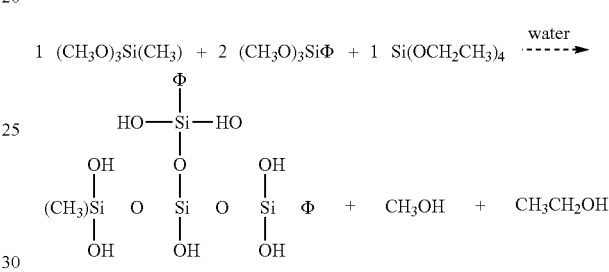

One can also provide a material having the formula:

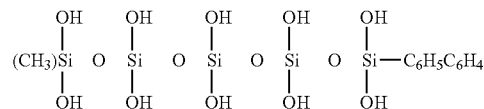

by hydrolyzing the components 1 $(CH_3O)_3Si(CH_3)$, 3 $Si(OCH_2CH_3)_4$ and 1 $(CH_3O)_3Si$—$C_6H_5C_6H_4$.

A preferred material is

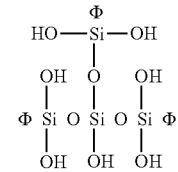

The materials are liquids as prepared. In some cases, if preferred, the by-produced alcohols and any residual water can be removed to provide a solid material, and in some cases the solid material is hard and appears to be almost crystalline and in some cases, the material is waxy or paste-like.

For use as lubricant coating materials, the polysilicates are combined with a condensation catalyst and allowed to cure on the appropriate substrate. The cured coating has lubricant properties.

EXAMPLES

Several samples of materials were provided by the same general procedure which was the following. The appropriate silanes and tetraethylorthosilicate (TEOS) were mixed at room temperature along with a stoichiometric amount, or less than a stoichiometric amount of water to hydrolyze the alkoxy groups present in the silane and polysilicate. The pH was adjusted as shown on the table using NaOH.

The mixtures were allowed to hydrolyze for about one hour.

The following formulas were used as shown in Table I

TABLE I

| Sample # | mw | 1 | 2 | 3 |
|---|---|---|---|---|
| TEOS | 208 | 2.08 | 2.08 | 2.08 |
| Φtms | 196 | 3.96 | 5.94 | 5.94 |
| tΦms | 234 | | | |
| H$_2$O pH = 10 | 18 | 1.8 | 1.17 | 3.6 |
| Ratio moles | | | | |
| Teos/silane | | 1.0/2.0 | 1.0/3.0 | 1.0/3.0 |
| Solution | | Hazy | clear | cloudy |

TEOS = Tetraethylorthosilicate
Φtms = phenyltrimethoxysilane
tΦms = triphenylmethoxysilane
1. - cable lubricant
2. —o—
3. hardened to a precipitate upon standing.

What is claimed is:

1. A composition of matter having the average general formula:

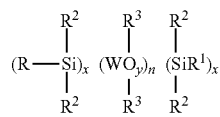

wherein the average molar ratio of x:y:z is 0.25-3:4:0.25-3, W is independently selected from the group consisting of Si, Ti, and Zr, and Al; wherein each $R^1$ is an aryl group with the proviso that there is present at least one $R^1$ group; R is independently selected from the group consisting essentially of $R^1$, alkyl groups having 1 to 8 carbon atoms, each $R^2$ is independently selected from a hydroxyl group, an alkoxy group having 1 to 8 carbon atoms, or an

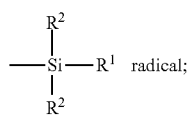

$R^3$ is independently selected from the group consisting of hydrogen, alkyl groups having 1 to 8 carbon atoms, or an

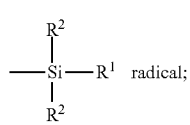

y has a value of 3 or 4;
s has an average value of about 1 to 5;

wherein WO$_y$ is derived from W(OR$^3$)$_4$, or W(OR$^3$)$_3$, wherein (OR$^3$) is independently selected from the group consisting of —OCH$_3$, —OCH$_2$CH$_3$, —OCH(CH$_3$)$_2$, —O(CH$_2$)$_3$CH$_3$, —OCH$_2$CH(CH$_3$)$_2$, —O(2-ethylhexyl), acetoxy, and, oximo.

2. A water solution of the composition of claim 1.

3. A water-alcohol solution of the composition of claim 1.

4. An alcohol solution of the composition of claim 1.

5. A composition of matter as claimed in claim 1 having the average formula

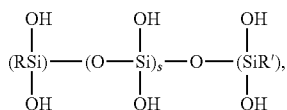

wherein, has an average value of from 1 to 5.

6. A composition of matter as claimed in claim 1 having the average formula

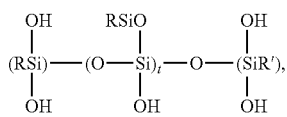

wherein t has an average value of from 1 to 5.

7. A composition of matter as claimed in claim 1 having the average formula

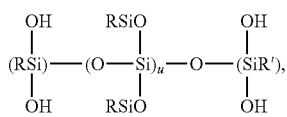

wherein u has an average value of from 1 to 5.

8. A composition of matter as claimed in claim 1 having the average formula

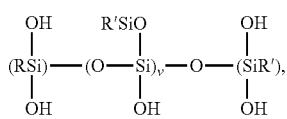

wherein v has an average value of from 1 to 5.

9. A composition of matter as claimed in claim 1 having the average formula

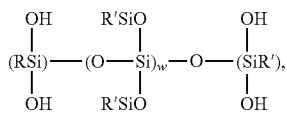

wherein w has an average value of from 1 to 5.

10. A composition of matter as claimed in claim 1 having the average formula

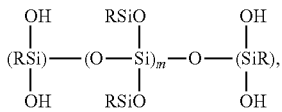

wherein m has an average value of from 1 to 5.

11. A composition of matter as claimed in claim 1 having the average formula

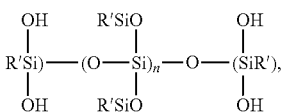

wherein n has an average value of from 1 to 5.

12. A composition of matter as claimed in claim 1 having the average general formula:

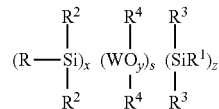

wherein the average molar ratio of x:y:z is 0.25-3:4:0.25-3, W is independently selected from the group consisting of Si, Ti, and Zr, and Al;

wherein each $R^1$ is independently selected from the group consisting of phenyl, xenyl, benzyl, and tolyl, with the proviso that there is present at least one $R^1$ group;

wherein each $R^3$ is independently selected from the group consisting of $R^1$ or hydroxyl, or alkoxy having 1 to 4 carbon atoms;

R is selected from the group consisting essentially of $R^1$, alkyl groups having 1 to 8 carbon atoms, each $R^2$ is a hydroxyl group or an alkoxy group having 1 to 8 carbon atoms;

$R^4$ is independently selected from the group consisting of hydrogen, alkyl group of 1 to 8 carbon atoms and the

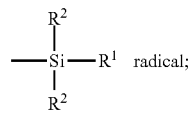

y has a value of 3 or 4;

s has an average value of about 1 to 5;

wherein $WO_y$ is derived from $W(OR^3)_4$, or $W(OR^3)$, wherein $(OR^3)$ is independently selected from the group consisting of i. —$OCH_3$,
ii. —$OCH_2CH_3$,
iii. —$O\,CH(CH_3)_2$,
iv. —$O(CH_2)_3CH_3$,
v. —$OCH_2CH(CH_3)_2$,
vi. —$O(2\text{-ethylhexyl})$,
vii. acetoxy, and,
viii. oximo.

13. A composition as claimed in claim 12 having the general formula:

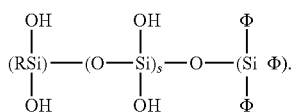

14. A composition as claimed in claim 12 having the general formula

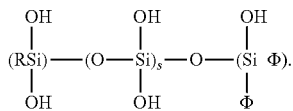

15. The composition as claimed in claim 1 wherein the composition is cured.

16. The composition as claimed in claim 12 wherein the composition is cured.

* * * * *